(12) United States Patent
Lu et al.

(10) Patent No.: US 10,678,328 B2
(45) Date of Patent: Jun. 9, 2020

(54) AUTOMATIC RADIOLOGY READING SESSION DETECTION

(71) Applicant: KONINKLIJKE PHILIPS N.V., Eindhoven (NL)

(72) Inventors: Kongkuo Lu, Briarcliff Manor, NY (US); Yuechen Qian, Lexington, MA (US); Eric Cohen-Solal, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 13 days.

(21) Appl. No.: 15/535,926

(22) PCT Filed: Nov. 30, 2015

(86) PCT No.: PCT/IB2015/059196
§ 371 (c)(1),
(2) Date: Jun. 14, 2017

(87) PCT Pub. No.: WO2016/097909
PCT Pub. Date: Jun. 23, 2016

(65) Prior Publication Data
US 2018/0039326 A1 Feb. 8, 2018

Related U.S. Application Data

(60) Provisional application No. 62/092,411, filed on Dec. 16, 2014.

(51) Int. Cl.
*G06F 3/048* (2013.01)
*G06F 3/01* (2006.01)
(Continued)

(52) U.S. Cl.
CPC .............. *G06F 3/013* (2013.01); *A61B 5/055* (2013.01); *A61B 5/742* (2013.01); *A61B 6/463* (2013.01);
(Continued)

(58) Field of Classification Search
CPC ........ G06F 3/013; G06F 19/00; G06F 19/321; G06F 3/038; G06F 3/04815;
(Continued)

(56) References Cited

U.S. PATENT DOCUMENTS 8,165,368 B2   4/2012   Vijaykalyan et al.
8,290,227 B2   10/2012  Chen et al.
(Continued)

FOREIGN PATENT DOCUMENTS

JP   2004261300   9/2004
JP   2013215223   10/2013
JP   2014124315   7/2014

*Primary Examiner* — Linh K Pham

(57) ABSTRACT

A system and method selects a user interface. The method is performed by an imaging device including a gaze tracker. The method includes receiving captured data used to generate an image that is displayed where the image includes identified areas. The method includes tracking a first viewing location on the image by a user of the imaging device. The method includes determining one of the identified areas in the image being viewed based upon the first viewing location. The method includes determining a first user interface to be provided based upon a first correlation to the determined identified area. The method includes displaying the first user interface for use by the user.

11 Claims, 6 Drawing Sheets

(51) Int. Cl.

| | | |
|---|---|---|
| *G16H 40/63* | (2018.01) | |
| *G01R 33/56* | (2006.01) | |
| *G02B 27/00* | (2006.01) | |
| *G06F 3/0481* | (2013.01) | |
| *A61B 6/00* | (2006.01) | |
| *A61B 5/055* | (2006.01) | |
| *A61B 5/00* | (2006.01) | |
| *G01R 33/54* | (2006.01) | |
| *G06F 3/0484* | (2013.01) | |
| *A61B 3/113* | (2006.01) | |

(52) U.S. Cl.
CPC ............ *A61B 6/467* (2013.01); *G01R 33/543* (2013.01); *G01R 33/5608* (2013.01); *G02B 27/0093* (2013.01); *G06F 3/0481* (2013.01); *G06F 3/04845* (2013.01); *G16H 40/63* (2018.01); *A61B 3/113* (2013.01)

(58) Field of Classification Search
CPC .... G06F 19/325; G06F 3/017; G06F 3/04842; A61B 2017/00216; A61B 6/469; A61B 6/5217; A61B 8/00; A61B 8/5223
See application file for complete search history.

(56) References Cited

U.S. PATENT DOCUMENTS

| | | | |
|---|---|---|---|
| 8,696,121 | B1 | 4/2014 | Fram |
| 9,144,407 | B2 | 9/2015 | Nakamura |
| 2006/0109237 | A1 | 5/2006 | Morita et al. |
| 2006/0109238 | A1* | 5/2006 | Lau .................. G06F 3/013 345/156 |
| 2007/0280508 | A1* | 12/2007 | Ernst ................ G06K 9/00624 382/107 |
| 2008/0062383 | A1 | 3/2008 | Emdroljpvslo et al. |
| 2010/0231504 | A1 | 9/2010 | Bloem et al. |
| 2011/0270123 | A1* | 11/2011 | Reiner ................ A61B 3/113 600/558 |
| 2013/0021336 | A1 | 1/2013 | Tsukagoshi et al. |
| 2014/0062865 | A1 | 3/2014 | Fateh |
| 2014/0098116 | A1 | 4/2014 | Baldwin |
| 2014/0146156 | A1 | 5/2014 | Strombom et al. |
| 2014/0236010 | A1 | 8/2014 | Nakano |
| 2015/0071405 | A1 | 3/2015 | Jacobs et al. |
| 2017/0242481 | A1* | 8/2017 | Lu ........................ G06F 3/013 |

* cited by examiner

AUTOMATIC RADIOLOGY READING SESSION DETECTION

CROSS-REFERENCE TO PRIOR APPLICATIONS

This application is the U.S. National Phase application under 35 U.S.C. § 371 of International Application No. PCT/M2015/059196, filed on Nov. 30, 2015, which claims the benefit of U.S. Provisional Application No. 62/092,411, filed on Dec. 16, 2014. This application is hereby incorporated by reference herein.

An imaging device is used to visualize internal structures of a body. For example, the imaging device may use nuclear magnetic resonance to image nuclei of atoms inside the body. The data gathered from using this technique may provide a basis from which an anatomical image may be generated. Specifically, a cross sectional, axial image of internal structures of the body may be represented in the image. The image may be used by a user such as a physician, technician, etc. to determine whether the internal structures captured in the image are healthy, injured, etc. by determining whether any anomalies are present.

An application may be configured to show the image to the user. The application may provide a user interface by which the user interacts with the image. Initially, the application may determine the body part(s) that is included in the image to determine the features to be included in the user interface. However, those skilled in the art will understand that the image may be for a variety of different body parts including organs, tissues, etc. and that the image may include one or more types of these body parts. For example, when the image is an axial slice of the human body particularly within a torso region, there may be a plurality of organs that are included in the image. Accordingly, the application may provide a general user interface in which the user may manually select the organ or tissue being viewed such that the appropriate specific user interface is provided. That is, the ultimate user interface to be used is based partially upon information from the image, but primarily from a manual user input.

Furthermore, within a single image, the user may require a different user interface for the various body parts that are shown in the image. That is, the user may require a first interface for a first body part and then may require a second interface for a second body part within the same image. In other words, there may be a first session for the first body part and a second session for the second body part. The user would be required to manually provide each input to utilize the different user interfaces in each session. In addition, the user may be shown a further image which may be part of an original session or part of a new session. When the further image is shown, the application may reset such that the general user interface is shown or the same specific user interface may be retained. However, the user may require the same user interface or may require a further user interface. When the general user interface is again shown for either scenario, the user is required to manually enter the input to bring up the specific user interface. When the further user interface is required when the same specific user interface is retained from the previous image, the user is also required to manually enter the input to bring up the further user interface.

Accordingly, it is desirable to determine which user interface should be provided for a given image and also determine when a session is being continued or when a new session is beginning.

The exemplary embodiments relate to a system and method for selecting a user interface. The method performed by an imaging device including a gaze tracker comprises receiving captured data used to generate an image that is displayed, the image including identified areas; tracking a first viewing location on the image by a user of the imaging device; determining one of the identified areas in the image being viewed based upon the first viewing location; determining a first user interface to be provided based upon a first correlation to the determined identified area; and displaying the first user interface for use by the user.

FIGS. 3A-D show images generated by the imaging device according to the exemplary embodiments.

Figure 4A:
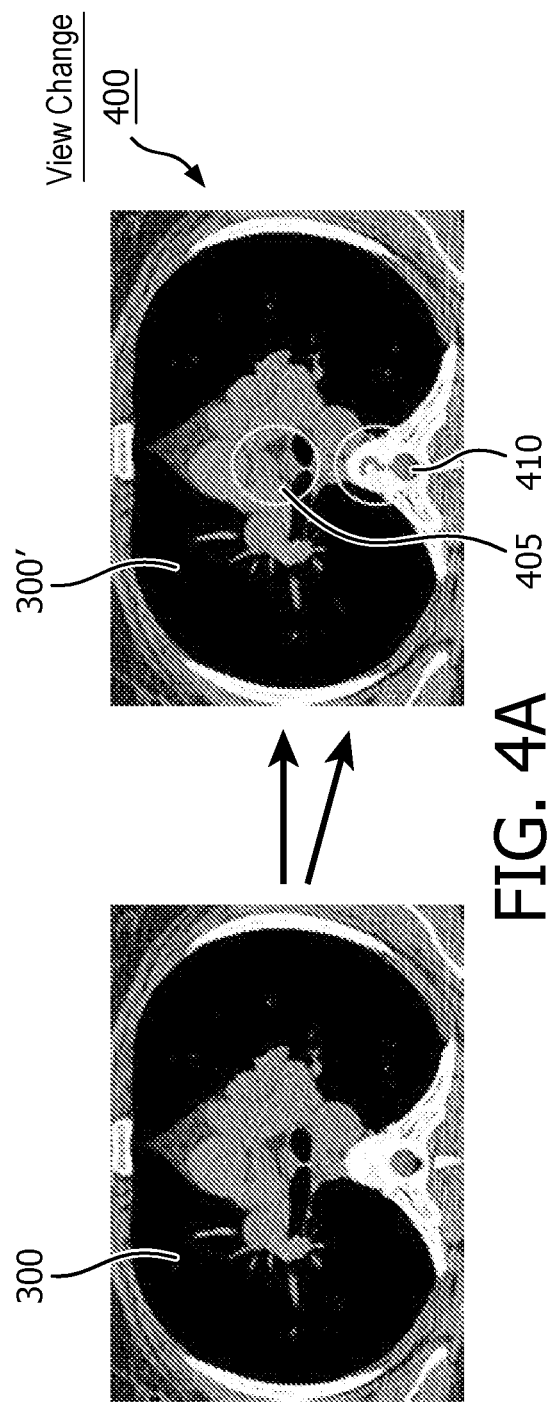
Figure 4B:
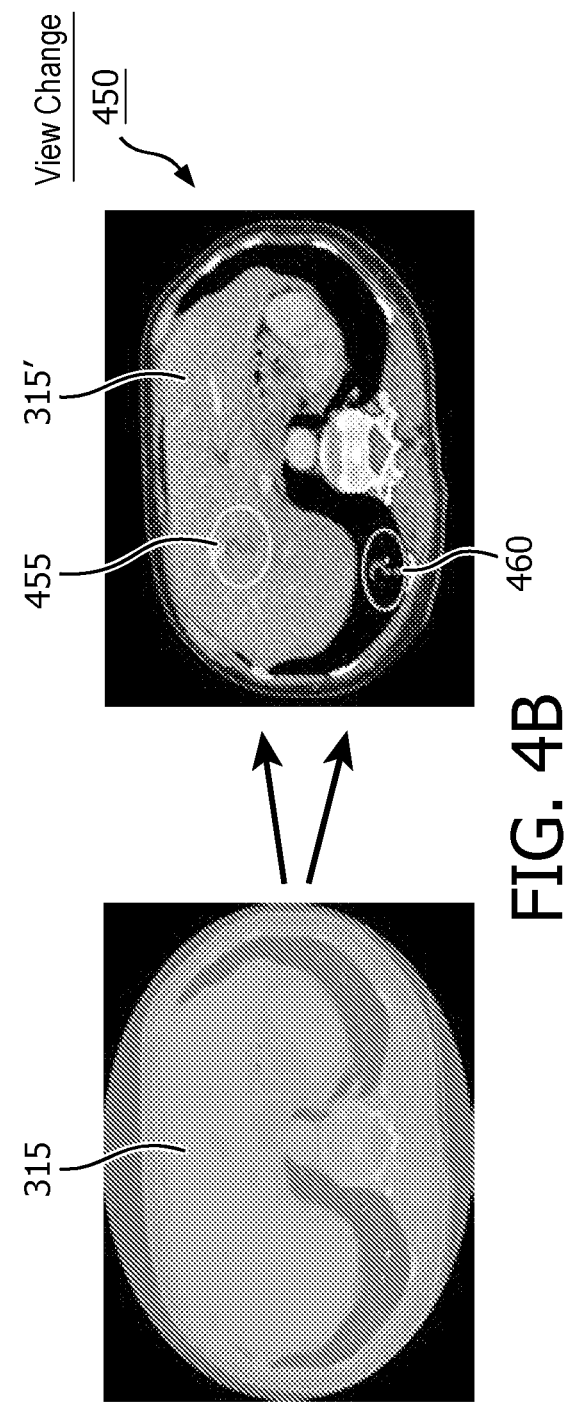

FIGS. 4A-B show view changes on images generated by the imaging device according to the exemplary embodiments.

Figure 5A:
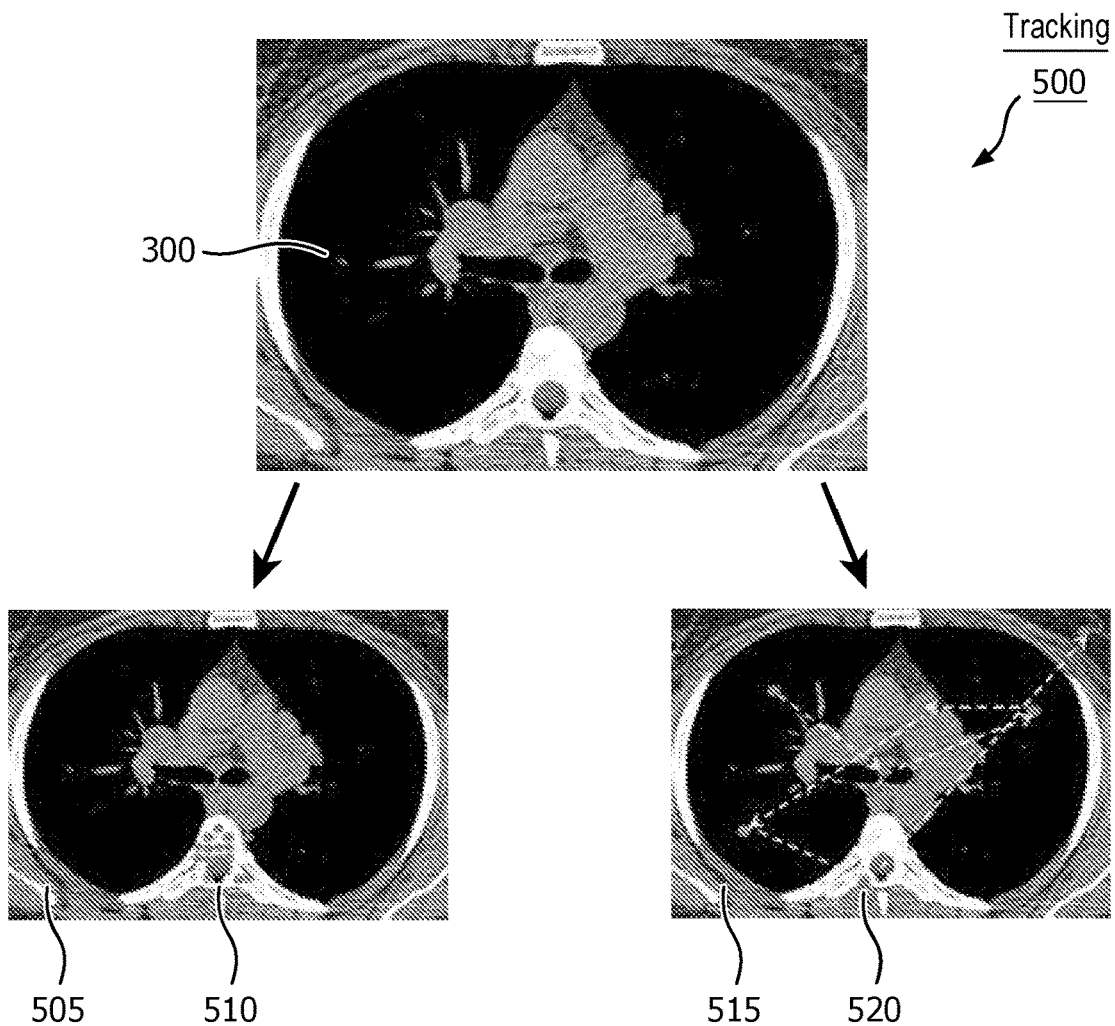
Figure 5B:
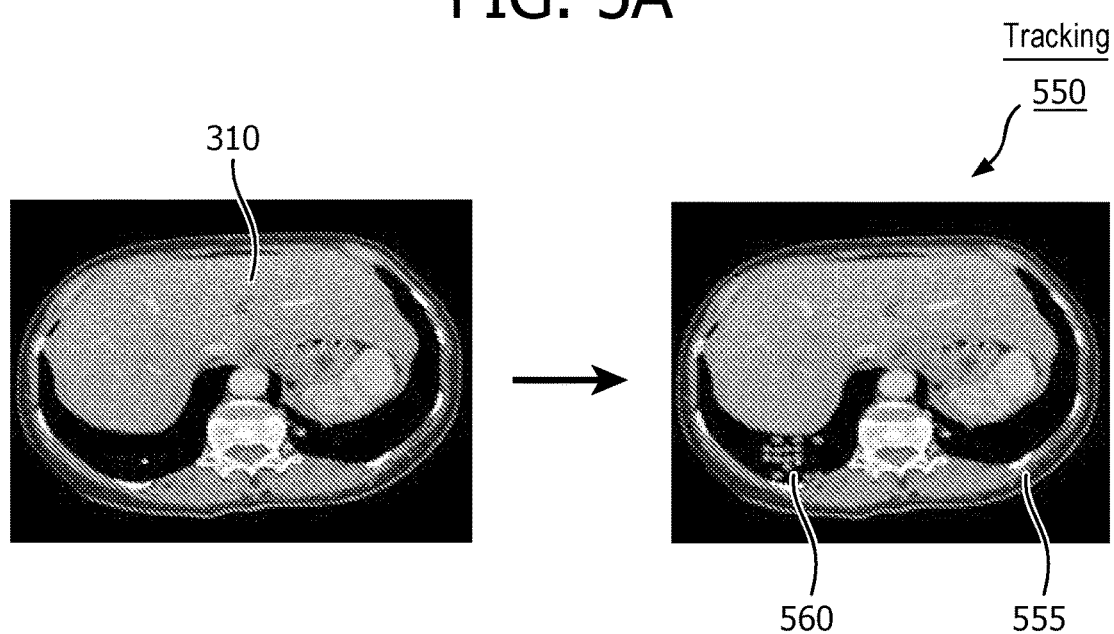

FIGS. 5A-B show view tracking of a user on images generated by the imaging device according to the exemplary embodiments.

Figure 6:
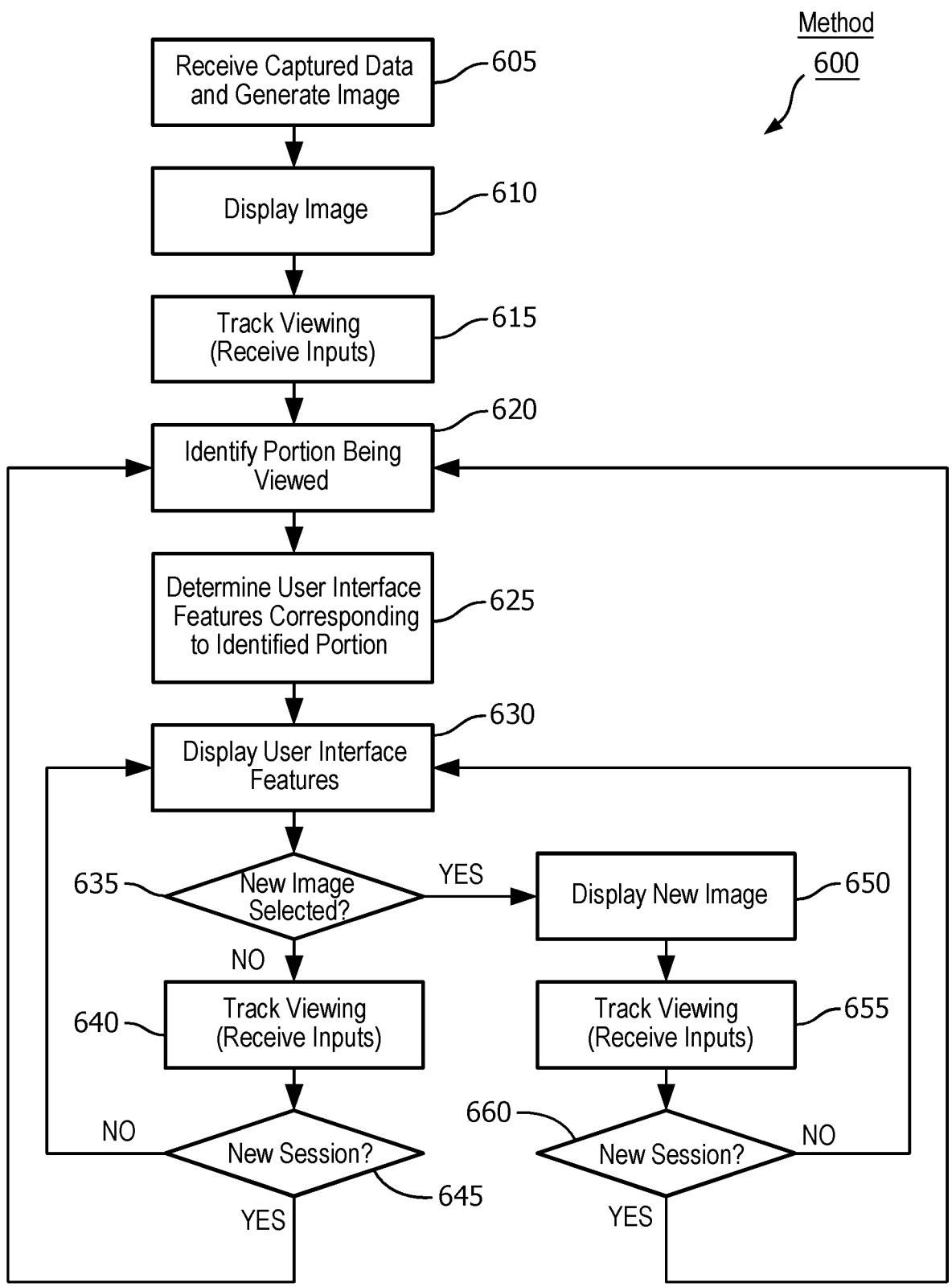

FIG. 6 shows a method of providing a user interface according to the exemplary embodiments.

The exemplary embodiments may be further understood with reference to the following description of the exemplary embodiments and the related appended drawings, wherein like elements are provided with the same reference numerals. The exemplary embodiments are related to a system and method of determining a user interface to be provided to a user of an imaging device that receives information from a capturing device to generate images. Specifically, the user interface may be determined based at least in part on a gaze detection of a location on the image which the user is viewing. Accordingly, the user interface may be properly provided for a given session. The imaging procedure and the devices therefor, the user interface, the gaze detection, the session, and a related method will be explained in further detail below.

Figure 1:
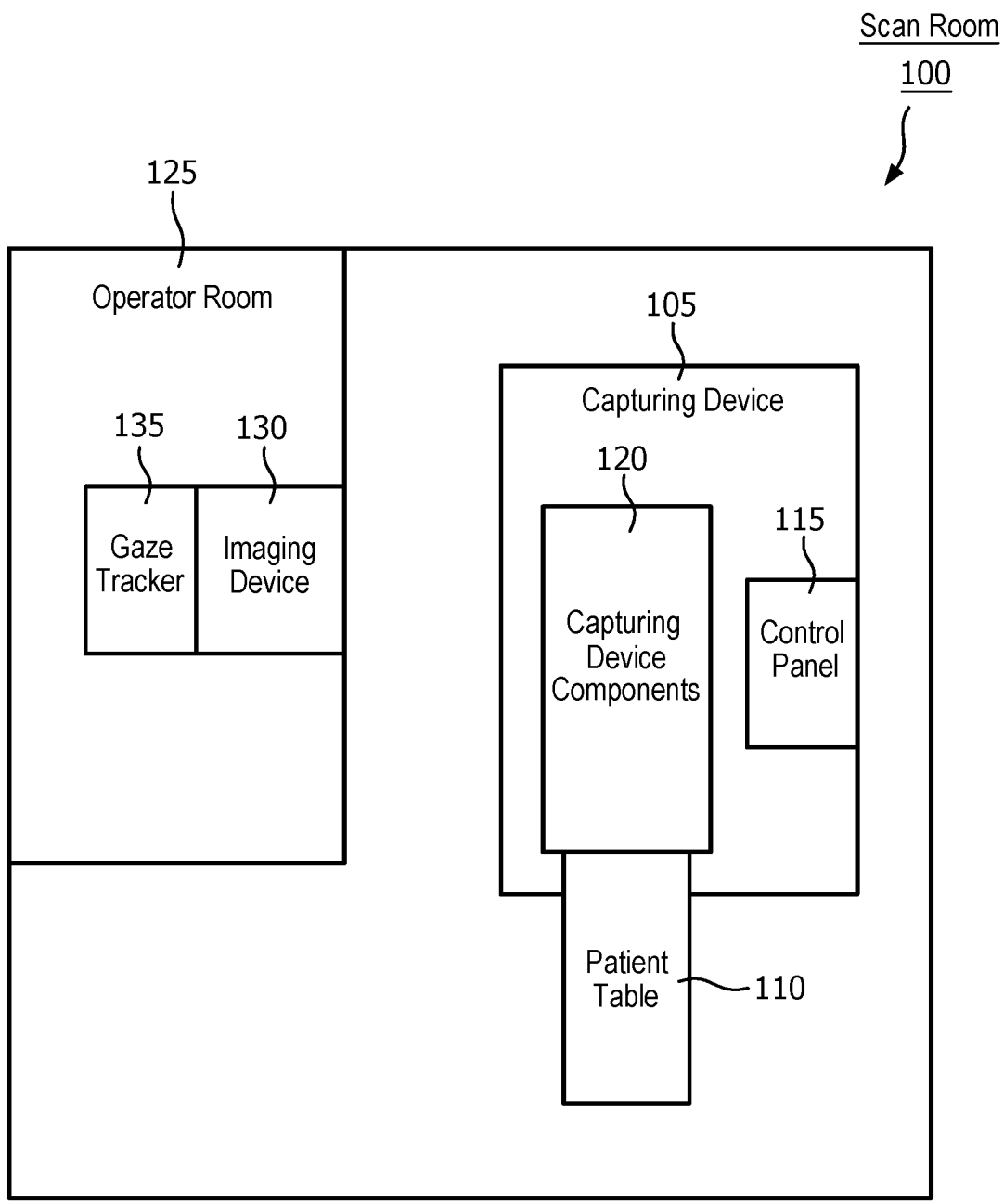
FIG. 1 shows a system for a scan room according to the exemplary embodiments.

FIG. 1 shows a system for a scan room 100 according to the exemplary embodiments. The scan room 100 is used for a patient who requires an imaging to be performed. For example, the patient may require a magnetic resonance imaging (MRI) image to be generated by performing a capturing procedure on a specific body portion. The scan room 100 includes a capturing device 105 which has a patient table 110, a control panel 115, and capturing device components 120 as well as an operator room 125 including an imaging device 130.

According to the exemplary embodiments, the capturing device 105 may perform a capturing procedure such as a scan in which data is gathered from the corresponding mechanism of the capturing procedure and transmitted to the imaging device 130. The capturing procedure may be performed by having a patient lie on the patient table 110 and utilize the capturing device components 120 to perform the scan. The patient may be moved within a bore of the capturing device 105 via inputs received on the control panel 115. The control panel 115 may allow an operator to move the patient table 110 for an alignment to be performed where the patient table 110 is moved to the isocenter (the point in space through which the central beam of radiation is to pass).

With particular reference to the capturing device 105 being a MRI device, the MRI device includes the retractable patient table 110 in which the patient lies. The patient is moved within the bore of the MRI device. The capturing procedure to generate the information transmitted to the imaging device 130 entails generating a magnetic field using a large, powerful magnet that aligns the magnetization of some atomic nuclei in the body. Radio frequency magnetic fields are applied to systematically alter the alignment of this magnetization. This causes the nuclei to produce a rotating magnetic field detectable by a component such as a scanner or receiving coils. This information is recorded and transmitted to the imaging device 130 to construct an image of the scanned area of the body.

Accordingly, when the capturing device 105 is a MRI device, the capturing device components 120 may include the magnet, gradient coils, radio frequency (RF) coils, and a sensor/RF detector/receiving coils. The magnet produces a strong magnetic field around an area to be imaged for the imaging procedure. This magnetic field allows nuclei (e.g., hydrogen nuclei of water molecules) to align with a direction thereof. The gradient coils may be disposed within the magnet to produce a gradient in the magnetic field in various directions (e.g., X, Y, and Z). The RF coil may be disposed within the gradient coils to produce a further magnetic field necessary to rotate the spins by various angles (e.g., 90°, 180°, etc.) selected by a pulse sequence. Thus, a radio frequency signal emitted by excited hydrogen atoms in the body may be detected using the energy from the oscillating magnetic field applied at the appropriate resonant frequency. The orientation of the image may be controlled by varying the magnetic field produced by the magnet using the gradient coils and a contrast between tissues is determined by a rate at which the excited nuclei return to an equilibrium state. Specifically, the RD detector may receive these energy measurements and provide the data to the imaging device 130 for processing to ultimately generate the images of the scan.

Figure 2:
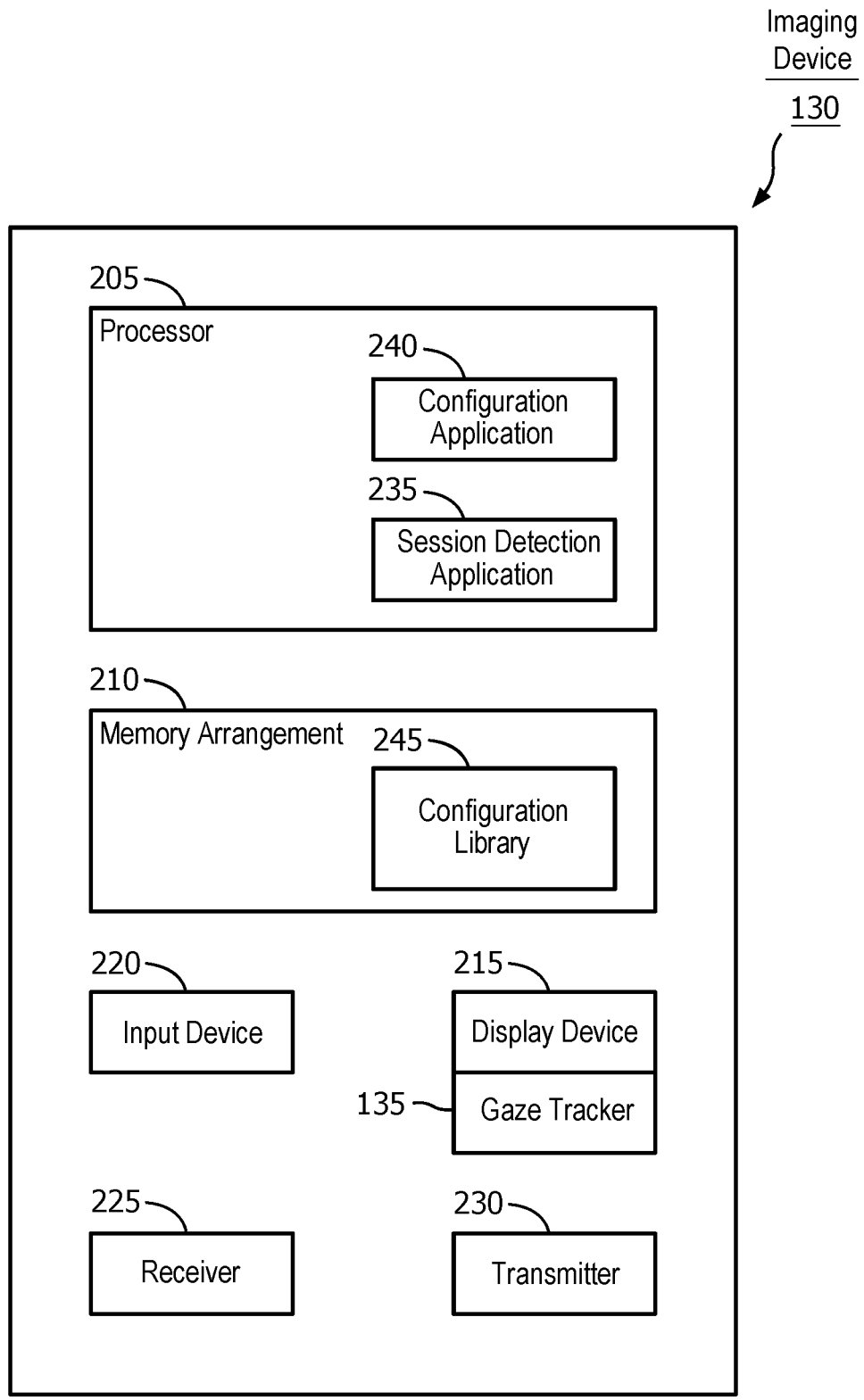
FIG. 2 shows an imaging device according to the exemplary embodiments.

Using the above capturing procedure, the imaging device 130 may be capable of generating the image. FIG. 2 shows the imaging device 130 of FIG. 1 according to the exemplary embodiments. The imaging device 130 may be configured to communicate using a wired or wireless arrangement with the capturing device 105. Accordingly, the imaging device 130 may include a receiver 225 and a transmitter 230 that may include the corresponding communication arrangement. However, it should be noted that the imaging device 130 may include a combined transceiver to provide the functionalities of the receiver 225 and the transmitter 230. The receiver 225 and the transmitter 230 may be for a short range wireless communication (with the capturing device 105 within a predetermined range) or for long range wireless communications such as with a network.

The imaging device 130 may include a processor 205 and a memory arrangement 210. The processor 205 may execute a session detection application 235 that determines when a new session is started. As will be described in further detail below, while the user is viewing the image generated by the imaging device 130, a first body part may be viewed which is indicative of a first session and subsequently a second body part may be viewed which is indicative of a second session. The processor 205 may further execute a configuration application 240 that determines an appropriate user interface to provide for a particular session. As will be described in further detail below, a given body part may have different functionalities associated therewith. Thus, the session relating to a particular body part may also entail selection of a proper user interface. The various user interfaces and selection criteria may be stored in the memory arrangement 210 as a configuration library 245.

The imaging device 130 may also include a display device 215 and an input device 220. For example, the processor 205 may also execute an image generation application that utilizes the data received from the capturing device 105 (via the receiver 225) to generate the images of the scan. These images may be shown on the display device 215. The images may also be shown one at a time or multiple images concurrently. The image generation application and/or the user interface may provide the user with a selection in the manner of how the images are to be shown as well as a layout for when multiple images are shown. The input device 220 may receive inputs from the operator to control operation of the capturing device components 120 to select a slice to be scanned for the image to be generated. As will be described in further detail below, the input device 220 may further receive inputs based upon a user interface that is provided and shown on the display device 215. For example, the input may indicate the number of images to be shown or a selection of an image to be shown. The inputs may further relate to information used in selecting the user interface.

The exemplary embodiments relate to development of an intelligent system for assisting in radiology reading and diagnosis. Accordingly, the exemplary embodiments further relate to gathering adequate information to estimate or detect intents of the user for processing a case. The user intent detection process may be launched in a variety of different stages. In a first example, the user intent detection process may incorporate retrospective features in which inputs received from the user provide a basis in which a user interface is provided. In a second example, the user intent detection process may incorporate proactive features in which the user interface is provided in a dynamic manner based upon currently available information.

Figure 3A:
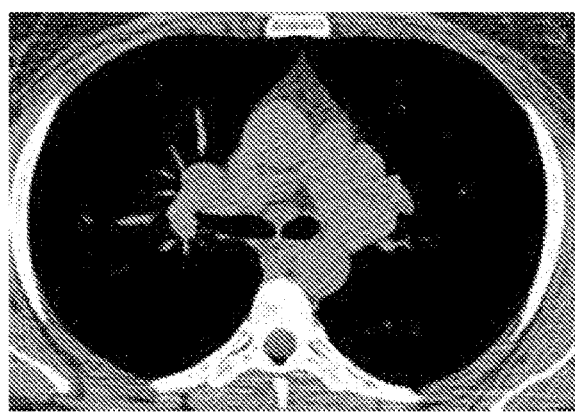
Figure 3B:
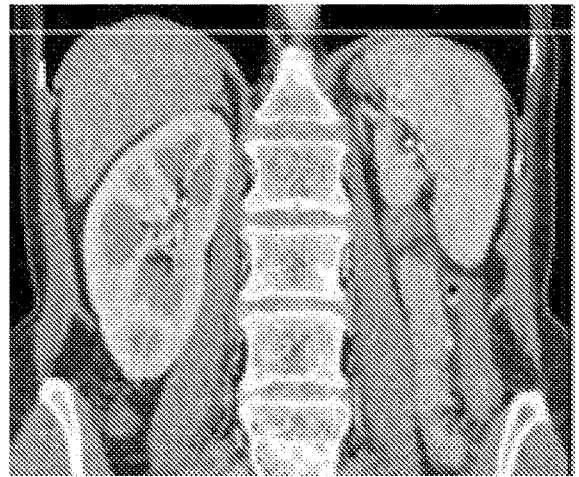
Figure 3C:
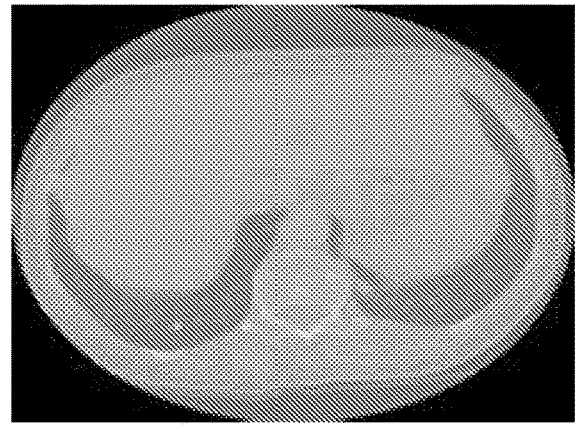
Figure 3D:

FIGS. 3A-D show images generated by the imaging device 130 according to the exemplary embodiments. The images shown in FIGS. 3A-D may be those in which the exemplary embodiments are directed. FIG. 3A shows an image 300 regarding a mediastinal window and axial slice. Those skilled in the art will understand that this image may include various body parts such as lungs and bone. FIG. 3B shows an image 305 regarding a lung and abdomen and further including bones. FIG. 3C shows an image 310 also of a lung and abdomen utilizing a different cross sectional view. FIG. 3D shows in image 315 further of a lung and abdomen utilizing a different slice in a common cross sectional view as the image 310 of FIG. 3C. The images 300-315 will be described in further detail below in their relationship with the exemplary embodiments.

With regard to the retrospective approach, the session is observed by tracking interactions that the user performs during a reading. For example, while viewing an initial view of the image, the user may change a window level, change an image frame, view various portions or whole images as a slice scroll pattern, review a case reading, etc. This information may be used retrospectively by the imaging device 130. However, those skilled in the art will understand that even in a retrospective approach, the imaging device 130 may not provide an appropriate response given this limited set of information. For example, when reading a chest region, the user may use the same window level (e.g., mediastinal (soft-tissue) window) to investigate a central mediastinal area for lymph nodes or spine within a similar image frame range or slice range. That is, the parameters may not be sufficient to uncover an actual reading flow which may also be dependent upon the particular user case. These aspects included within the reading of the image may utilize different user interfaces. As such, the imaging device 130 may be incapable of determining with a sufficiently high probability that one user interface is more appropriate than the other.

With regard to the proactive approach, during the image reading and initial diagnosis stage, the process of analyzing the image may be more efficient from providing the correct user interface for a body part being viewed which may constitute a session. That is, detecting a session of a reading may be determined at this stage. The reading session may be defined with a variety of factors. In a first factor, the session may be defined based upon a detectable time period during which the user is actively looking for findings in the image. In a second factor, the anatomical body part is involved such as a rough body region (e.g., head, chest, abdomen, etc.), an organ (e.g., lungs, liver, kidney, etc.), an anatomical structure (e.g., spine, bony structure, etc.), etc. Those skilled in the art will understand that further factors may also be involved. If a session may be detected or predicted at the onset of the session, the imaging device 130 may use the session information to allocate visualization, diagnosis, informatics resources, etc. to facilitate viewing and associated processing. In a particular example, the proper user interface may be provided without significant user intervention (e.g., manual selection of the user interface).

It should be noted that the exemplary embodiments are focused upon providing the correct user interface for any given session. For example, a minimal amount of information that provides a highest probable user interface may be performed by the configuration application 240. Therefore, the reactive approach of the exemplary embodiments may be used by itself, the proactive approach of the exemplary embodiments may be used by itself, or a combination thereof may be used, if required.

The exemplary embodiments particularly relate to utilizing the proactive approach to provide the user interface prior to a user being required in any way to manually select the desired user interface. Furthermore, the exemplary embodiments intend to eliminate as much manual user intervention necessary to provide the correct user interface. That is, the user may need to only use the imaging device 130 in a standard manner which enables the configuration application 240 to select the user interface based upon the user intent detection process. The exemplary embodiments therefore utilize a gaze tracking.

The gaze tracking functionality may be performed by a gaze tracker 135. The gaze tracker 135 may be a component that is incorporated with the imaging device 130, incorporated with the display device 215, coupled in a modular fashion with either the imaging device 130 or the display device 215, configured as a separate component that is communicatively connected to the imaging device 130 (e.g., via the receiver 225), etc. In a particular exemplary embodiment, the gaze tracker 135 may be a portable system that is attached to and calibrated for a work station such as the imaging device 130.

The gaze tracker 135 may include a variety of components that enable sufficiently accurate locations of gaze points or locations on the image being shown on the display device 215. For example, the gaze tracker 135 may have components that track a movement of an eye of the user to estimate a gaze location based upon a known distance between the image being viewed and the eye. The gaze tracking and detected gaze locations may be used alone or in combination with preliminary underlying visual content information to improve a reading session detection and enable session detection in near real time. More specifically, this session detection may enable a selection of a user interface associated with the session. As will be described in further detail below, when a reading consists of separate sessions, the gaze tracking may be used to detect a change in the viewing location by detecting basic fixations or fixation clusters and correlating them with underlying content using image processing methods to detect whether there is significant change of underlying visualization content (e.g., above a predetermined threshold of change). The gaze tracking may also be used to confirm a starting point of a session or a new session if a session is already in progress by detecting a viewing pattern of the user (e.g., transition period between two sessions where user performs a visual survey mode rather than a focused reading).

To further guarantee that an appropriate action (e.g., selection of a user interface) has a higher probability of success, the exemplary embodiments may utilize other interactions such as those performed by the user during an ordinary course of viewing the images. For example, a window level change or slice scrolling activities may also be utilized as information that forms the basis of the action. Such actions may be used in detecting hidden sessions corresponding to actual visual tasks. This may enable the configuration application 240 to dynamically prioritize information or tools that is presented to the users or anticipating a need for specific resources such as user interfaces.

It should be noted that the use of the gaze tracker 135 that tracks a movement of an eye is only exemplary. Those skilled in the art will understand that the exemplary embodiments may utilize other components that may track or detect viewing locations. For example, if the display device 215 is a touchscreen, the user may place a finger on the area of the intended viewing. Those skilled in the art will further understand that the gaze tracker 135 may use a calibrating process for the user or setting in which the gaze tracker 135 is used. For example, the user may perform a preliminary calibration procedure in which an application registers a position of the eye upon viewing selected locations on the display device 215. Using this as the basis, the gaze tracker 135 may perform its functionalities described herein. When calibrated, this may be used for a given user, for a given setting, etc. or may be re-calibrated each time the imaging device 130 is used.

FIGS. 4A-B show view changes on images generated by the imaging device 130 according to the exemplary embodiments. Specifically, FIG. 4A shows a view change 400 for the image 300 of FIG. 3A and FIG. 4B shows a view change 450 for the image 315 of FIG. 3D. The view changes 400, 450 may illustrate when the user performs a survey view to a focused view. In FIG. 4A, the user may view the image 300 in its entirety. Subsequently, as shown in FIG. 300', the user may focus the view on different body portions shown in the image such as portion 405 (e.g., lung) or portion 410 (e.g., bone). A substantially similar viewing may be performed in the view change 450 where a survey view is done and a focus view is subsequently done in portion 455 or portion 460.

As discussed above, with only inputs provided from the user (e.g., slice change), the imaging device 130 may be incapable of correctly determining the body part that is being viewed. For example, in the view change 400, the user may focus on either the portion 405 or the portion 410. Being different body parts and body part types, the imaging device 130 may not be capable of providing the correct user interface except for a generic one that may not include any of the predetermined functionalities respectively associated with each body part. However, the exemplary embodiments utilize the gaze tracker 135 to determine whether the portion 405 or the portion 410 is being viewed. In this manner, the configuration application 240 may receive the viewing information from the gaze tracker 135 to determine which portion is being viewed and reference the configuration library 245 to select the correct user interface.

The exemplary embodiments therefore integrate gaze tracking into a reading session detection process to determine an appropriate action such as selecting a user interface to be provided. The exemplary embodiments may further associate the image data and other user interactions to potentially increase a probability that the selected user interface is the one to be provided. Accordingly, the exemplary embodiments may include a variety of steps to enable this incorporation such as an integration, a calibration, a tracking, a selection, and a detection.

Initially, the gaze tracker 135 is integrated into the imaging device 130. Specifically, the hardware and software associated with the gaze tracker 135 are installed with the imaging device 130. As discussed above, the hardware of the gaze tracker 135 may be incorporated, attached in a modular manner, or utilized as a separate component with the imaging device 130. The software associated with the gaze tracker 135 may include the session detection application 235 and the configuration application 240 that are installed (e.g., stored on the memory arrangement 210 for execution by the processor 205). The hardware and software components may operate in conjunction with one another enabling a tracking of user gaze points and correlating gaze points with an underlying image or non-image content shown on the display device 215. Furthermore, there may be a user profile associated with each user that is maintained in a database and stored in the memory arrangement 210. As will be described in further detail below, the user profile may include calibration information.

The gaze tracker 135 may be calibrated for individual users prior to any use. As each user may have eye levels at different heights and distances from the image, the gaze tracker 135 may be required to be calibrated for each user to properly be configured to track the gaze points. That is, the angle in which the user views the image on the display device 215 may differ. In a first example, the calibration may be performed dynamically. This mode may be applied for a variety of times such as when a user is a first time user, a prior user is scheduled for a recalibration, a set schedule for a recalibration, etc. Thus, prior to a reading session beginning, the calibration may be performed such as in a manner discussed above. When a database of user profiles are maintained, the calibration information generated from this process may be stored. In a second example, the calibration may be performed in an "offline" manner. Specifically, the calibration may be performed outside the operations of the imaging device 130. The calibration information may be stored in a file or other format and may be loaded prior to the user associated with the calibration information beginning a reading session. This may also be loaded dynamically or when associated with a user profile. For example, with no user profile, the user may be prompted to perform the calibration prior to use or load previously stored calibration information. In another example, with a user profile, the user may load the profile and either use the previously stored calibration information or load the offline calibration information.

Once integrated and calibrated for the user, the gaze tracker 135 may be activated and continuously track the gaze locations of the user as a background operation. The gaze locations may be correlated with graphical representations shown on the display device 215 that correlate with underlying visual content. The tracked gaze points may be processed prior to use for subsequent processes such as tracking gaze locations on an image generated based upon information received from the capturing device 105. The processing of the tracked gaze points at this stage may provide information relating to smoothing, clustering, fixation detection, and fixation pattern detection. Those skilled in the art will understand that raw gaze points may be quite noisy. Therefore, if pre-processing is not provided by a tracking engine associated with the gaze tracker 135, a smoothing process may be necessary to eliminate the noise. A clustering of gaze points may provide meaningful relationships and/or connections with locations on the display device 215. For example, a cluster of gaze points may be determined such that any gaze location within the cluster area may be indicative of viewing in the general area as a whole. A fixation detection may relate to detecting a visual focus based upon clustering and gaze dwelling time at a particular location. A fixation pattern detection may relate to detecting meaningful focused investigation locations.

With the gaze tracker 135 integrated, a calibration for a particular user is performed, and a gaze tracking for pre-processing is also performed, a user may load an image that is generated from information received from the capturing device 105. Specifically, the user may select a patient case and apply proper hanging protocols to import image data that was generated and begin a reading session. As this may represent a first image that is shown on the display device 215, the session detection application 235 may also determine a start to a new session. The processor 205 may further be configured to execute a detection application with an associated detection library stored on the memory arrangement to detect anatomical structures that may be present in the image. When the anatomical structure detection application (e.g., algorithm, package, etc.) is available, the body part(s) that exists in the current image may be estimated or detected based upon, for example, Digital Imaging and Communications in Medicine (DICOM) tags. The anatomical structure detection application may also extract existing body part(s) and/or anatomical structure(s) in the image by applying image processing approaches to the image data.

It should be noted that the above selection process may provide a preliminary selection of potential actions that may be performed once a reading session is started. For example, with particular regard to the image 300 of FIG. 3A, the anatomical structure detection application may determine that a mediastinal window and axial slice is shown. A further determination may indicate that organs included in the slice may be lungs and bones. In this manner, the preliminary selection may relate to lungs and bones and may be further defined for actions associated with lungs and bones in this viewpoint. Therefore, the configuration application 240 may determine that the user interface that may be provided have this association.

Once the reading session begins, the session detection application 235 and the configuration application 240 along with the gaze tracker 135 may perform a variety of different functionalities. For example, activities or interactions of the user may be tracked. Specifically, the gaze tracker 135 may track the gaze locations of the user including gaze point cluster, fixation, and fixation cluster locations. FIGS. 5A-B show view tracking of a user on images generated by the imaging device 130 according to the exemplary embodiments. Specifically, FIG. 5A shows the image 300 with potential tracks. Specifically, in track 505, a gaze cluster 510 may be determined. Therefore, the configuration application 240 may determine that the user is viewing the bone in the image 300. As such, an appropriate action that may be performed is to provide the user interface associated with the identified bone in the image 300. In track 515, a plurality of fixation locations 520 may be determined. Therefore, the configuration application 240 may determine that the user is surveying the image 300 to determine any abnormalities or points of interest. Subsequently, the user may perform a gaze cluster 510 upon viewing the bone in the image 300. FIG. 5B shows the image 310 in which a track 555 is shown also having a gaze cluster 560.

It should be noted that the exemplary embodiments may be configured to determine the appropriate action based upon the above process alone. That is, the user interface that is to be provided may be based upon the pre-processing including the determined body parts in the image and the gaze tracking via the gaze tracker 135. However, as will be described in further detail below, the configuration application 240 may additionally utilize other related information.

As discussed above, the configuration application 240 may also track user interactions. In a first example, during the course of a session or reading, a window level of the slice or image may be determined. Specifically, the user may manually adjust a window level or apply different predefined windowing options to assist in the image reading such as a lung window that may be selected when the lungs are investigated. The window level may be indicative of a particular region in the image that the user wishes to focus. In a second example, during the course of a session or reading, an orientation of the image may be determined such as when a user switches among different multi-planar reconstruction visualization options including axial, coronal, sagittal, etc. The orientation may also be indicative of a particular region in the image that the user wishes to focus. In a third example, during the course of a session or reading, a slice and scroll pattern may be determined that indicates whether the user is reading backward or forward, whether there is a detectable change of slice scrolling speed, etc. In each of these examples, the configuration application 240 may also determine that the area from the window level, orientation, and/or slice and scroll pattern is of interest and the body part therein is also expected to be of interest.

Through combining the information gathered from the interactions provided by the user, the configuration application 240 may be capable of determining a proper action to be performed with a higher certainty. In the examples above, the gaze tracker 135 may have provided gaze tracking information on the image 300 that the lungs are being viewed (e.g., a gaze cluster located in the lung tissue of the image). The gaze tracking information may have indicated that there were a plurality of gaze locations in this area for a predetermined amount of time. The configuration application 240 may have also received the interaction information relating to window level, orientation, and/or slice and scroll pattern, all of which may also indicate that the lungs are the body part of interest. Therefore, the configuration application 240 may perform the proper action such as providing the user interface relating to lungs.

The exemplary embodiments may further be configured to determine when a session has ended and whether a new session has started via the session detection application 235. As discussed above, the session detection application 235 may be aware of when a new session starts for a user when an image is loaded to be viewed on the display device 215. The session detection application 235 may also determine that a new session starts when a variety of other conditions are present such as a user profile being loaded, calibration information being loaded, the gaze tracker 135 detecting a presence of a person in its field of vision, etc. The session detection application 235 may subsequently determine when a session has ended from obvious reasons such as the imaging device 130 being deactivated. However, the session detection application 235 may determine when a session ends and a new session begins for a given user during an overall time period.

The exemplary embodiments are configured for the session detection application 235 to be aware when a new session begins based upon being triggered by the gaze tracking and/or the user interaction. As discussed above, the user interaction may provide indications that a current session ends and a new session begins. Aside from obvious indications, the session detection application 235 may determine that certain user interactions are also indicia of a new session. In a first example, a user interaction such as a window level change or a slice change may be detected and suggest a potential new reading session. In a second example, a user interaction of a new image being loaded may be detected and suggest a potential new reading session. However, it should be noted that these user interactions may still relate to a common session. Specifically the user may be viewing a body part in a first image and perform a window level change or a slice change to better view the same body part or load a second image to view the same body part at a different orientation.

Accordingly, the exemplary embodiments are configured to utilize gaze tracking to determine when a new session begins. Initially, it is again noted that the session detection application 235 may use the gaze tracking as well as the user interaction to reach a conclusion as to whether a new session has begun. The session detection application 235 may determine the new session based upon a variety of factors and combinations thereof.

In a first example, the session detection application 235 may determine a new session based upon a change of anatomical content that is detected by analyzing underlying visual content associated with gaze tracking outcomes. A more certain time when this trigger is used is when a new image is loaded. However, this feature also incorporates portions being viewed to determine when a new session is started. Thus, even when a new image is loaded, if a common body portion is determined to be viewed in both images, the session detection application 235 may determine that the same session is being continued. For example, gaze point clusters, fixations, and fixation clusters may all be indicative of a common body portion being viewed. Contrarily, when a different body portion is being viewed in the same image or in a different image, the session detection application 235 may determine that a new session has indeed begun and may proceed accordingly (e.g., indicate to the configuration application 240 so that a new user interface is provided).

In a second example, the session detection application 235 may determine a new session based upon a viewing pattern that is checked to indicate whether the user is viewing the image without focusing attention (e.g., saccade or jump). That is, if there is a jump in the gaze tracking, the session detection application 235 may conclude that there is a transition between two sessions since, for example, two different body portions are being viewed. On the other hand, if a basic fixation or fixation cluster is detected on a new body part, this may also suggest a start of a new session (e.g., from a low intensity pixel area to a high intensity pixel area or from a lung to abdomen or liver if knowledge of anatomical structures is available.) If useful user interactions are also available, such information may be used to confirm the start of a new session.

In a third example, the session detection application 235 may determine a new session based upon gaze tracking associated with underlying visual content analysis. This may be used to determine whether the user is investigating a different anatomical region, whether visual searching during a transition of two sessions is detected, whether a new session actually starts, etc. Furthermore, using gaze-driven data and underlying anatomical structure analysis, a correlation of the reading session with anatomical region may be performed to determined whether a new session has started.

It should be noted that the above examples the session detection application 235 utilizes to determine whether a new session has started are only exemplary. Those skilled in the art will understand that there may be various other manners in which the gaze tracking may be used according to the exemplary embodiments to indicate when a new session has started. For example, a combination of the examples above within the gaze tracking, within the user interaction, and combined thereof may be used.

When a new session has begun (and is confirmed), the configuration application 240 may perform the above described process to determine the appropriate action to be performed such as providing a new user interface. That is, using image content information, associated with user interactions (if available), the configuration application 240 may detect the anatomical region relevant to the new session using the gaze tracking (e.g., head, chest, abdomen, etc.). If, however, the anatomical information is unavailable, the new session may still start and may be marked without anatomical content.

It should also be noted that if the anatomical information is not available, the user interface that is provided may be generic. Thus, when a current session using a specified user interface that was selected using the method described above by the configuration application 240 has ended, the session determination application 235 may determine that a new session may have begun with no anatomical information. The configuration application 240 may be configured to provide a generic user interface for the user to manipulate as desired.

The exemplary embodiments are further configured to capture user actions when presented with the user interface elements for the reading session detection from detecting a particular session. For example, if a reading session is detected and is related to the vascular system and a vascular user interface tool is offered to the user, the user may or may not utilize the provided user interface. This instance may be captured. Such instances may be captured over a period of time such that a large number of instances that are gathered may be considered as ground truth to separate instances where the tool was used from instances where the tool was not used. The dynamic gathering of ground truth that may be done for each individual user and also with groups of users may be used to refine an algorithm by determining with more precision through learning to observe what the optimal parameters are for a particular reading-session type. In this manner, the exemplary embodiments may utilize further information to improve upon the user experience.

FIG. 6 shows a method 600 of providing a user interface according to the exemplary embodiments. Specifically, the method 600 relates to an appropriate action to be performed using gaze tracking information. The method 600 will be described with regard to the capturing device 105 and the imaging device 130 of FIG. 1. However, it should be noted that the use of the medical application and capturing/imaging device is only exemplary. Those skilled in the art will understand that the exemplary embodiments may relate to any procedure in which gaze tracking may be used as a basis to determine further information, particularly regarding viewing sessions.

For purposes of this description, it may be assumed that the integration of the gaze tracker 135 and all accompanying hardware and software have been performed. It may also be assumed that the calibration of the gaze tracker 135 with the current user has also been performed. That is, all pre-processing procedures may be assumed to have been performed such as loading a user profile.

In step 605, the imaging device 130 receives captured data from the capturing device 105. As discussed above, the capturing device 105 may be a MRI device that generates magnetic resonance imaging data that is used by the imaging device 130 to recreate an image. Thus, the imaging device 130 may also generate the image to be shown to the user via the display device 215. In step 610, the image is displayed. When the first image is shown, the session detection application 235 may determine that a session has begun.

As discussed above, the imaging device 130 may also utilize anatomical information and libraries to determine any body parts that are included in the image. Thus, the processor 205 may perform image detection procedures and/or use the anatomical information that may be provided to associate the different areas of the image with correlated body parts.

In step 615, the gaze tracker 215 may track the viewing of the user. The gaze tracking of the user may indicate whether the user may be surveying the image or is focusing on a particular portion of the image such as with gaze clustering. If the configuration application 240 determine that a survey is being performed, the configuration application 240 may wait a predetermined amount of time prior to providing a fallback user interface such as a generic one. It should be noted that the configuration application 240 may receive the inputs being entered by the user such as those associated with image manipulation (e.g., window, slice, orientation, etc.). This information may also be used by the configuration application 240. Based upon this information, in step 620, the configuration application 240 determines the portion being viewed by the user.

In step 625, the configuration application 240 determines a user interface that is associated with the identified body portion included in the image that the user is viewing based upon the gaze tracking and/or other user input information (as well as any anatomical information that was available in the previous steps). If the configuration application 240 determines that a specific portion of the image is being viewed and it corresponds to a specific body portion, the configuration library 245 may be accessed and the specific user interface may be selected. However, if the configuration application 240 determines that a survey is being performed, the configuration application 240 may wait a predetermined time period to initially determine whether a focusing is performed or whether to provide a basic or generic user interface. Therefore, in step 630, the user interface is provided and displayed for use.

In step 635, the session detection application 240 determines whether a new image has been selected. If the same image is being viewed, the session detection application 240 continues the method 600 to step 640 in which the gaze tracking continues and any further user inputs are received. In step 645, the session detection application 240 determines whether a new session has begun. As discussed above, the session detection application 240 may determine whether a new session has begun based upon a variety of factors such as through gaze tracking, through user inputs, and a combination thereof. If the same session is being continued, the session detection application 240 returns the method 600 to step 630. However, if a new session is determined, the session detection application 240 returns the method 600 to step 620 for a new analysis to determine the appropriate action to be taken or user interface to be provided.

Returning to step 635, if the session detection application 235 determines that a new image has been selected, the session detection application 235 continues to step 650. In step 650, the new image is displayed and the gaze tracking is performed on this new image as well as any inputs that are entered for this new image. In step 660, the session detection application 235 determines whether a new session has begun. As discussed above, despite a new image being shown, it is possible for the same session to be continued with this new image. Again, the session detection application may use gaze tracking, user inputs, or a combination thereof to make this determination. If a new session has not started, the session detection application 235 returns the method 600 to step 630. However, if a new session has started, the session detection application 235 returns the method 600 to step 620.

It should be noted that the method 600 may include a variety of further steps such as those already discussed above. Furthermore, the identification of portions as well as determinations of sessions may include additional verification steps. That is, the body portion and the session start/end may be confirmed. This confirmation may be performed in a variety of manners such as with the gaze tracking information, user input information, manual indications provided, etc.

According to the exemplary embodiments, the system and method of the exemplary embodiments incorporate gaze tracking for reading sessions. From integrating a gaze tracker and calibrating the gaze tracker for a user, the gaze tracking may be used with other information to determine a location in an image being viewed. With available anatomical information, the location may be identified as correlating to a body portion such that subsequent actions may be performed such as providing a user interface tailored for the determined body portion. The gaze tracking may also be used as an indication of whether a current session has ended and a new session has begun or whether a current session is being continued.

The exemplary embodiments focus on detecting reading sessions associated with high-level anatomical regions such as head, neck, chest, and abdomen regions. Subsequently, sub-sessions may be detected as detailed as possible and may require additional information from image processing. Depending on the detail of the body part or anatomical structures that may be provided through image processing on imported patient image data, the underlying analysis of visual content and reading pattern correlated with detected and tracked gaze points may vary. For instance, if the anatomical structures, body parts, or organs are known, a correlation of the gaze/fixation point with a specific structure may be determined by checking whether there is a match of locations. If the information of anatomical structure detection is not sufficient, a basic intensity or shape based approach may be implemented to discover the viewing content using gaze tracking, fixation tracking, image data, and anatomical knowledge.

Those skilled in the art will understand that the above described exemplary embodiments may be implemented in any suitable software or hardware configuration or combination thereof. An exemplary hardware platform for implementing the exemplary embodiments may include, for example, an Intel x86 based platform with compatible operating system, a MAC platform and MAC OS, a mobile hardware device having an operating system such as iOS, Android, etc. In a further example, the exemplary embodiments of the above described method may be embodied as a program containing lines of code stored on a non-transitory computer readable storage medium that, when compiled, may be executed on a processor or microprocessor.

It will be apparent to those skilled in the art that various modifications may be made in the present invention, without departing from the spirit or the scope of the invention. Thus, it is intended that the present invention cover modifications and variations of this invention provided they come within the scope of the appended claims and their equivalent.

What is claimed is:

1. A method for supporting a visual image analysis, comprising:
   receiving, by an imaging device including a gaze tracker, captured data used to generate an image that is displayed, the image including identified areas;
   collecting gaze tracking information, by the imaging device via the gaze tracker, the gaze tracking information comprising a viewing location on the image by a user of the imaging device including determining a starting point of a session or a new session;
   determining, by the imaging device, one of the identified areas in the image being viewed based upon the viewing location;
   deriving a session state within a clinical context from at least a combination of two of: gaze tracking information, user interaction information, visual content analyses information; a user profile, interaction history or patient record data;
   determining, by the imaging device, a user interface to be provided based upon the determined identified area and the session state;
   displaying, by the imaging device, the user interface for use by the user; and
   capturing user actions on the user interface over a period of time, wherein the user actions include instances where the user interface is used and unused, and wherein the user actions are used to determine the user interface for a further session.

2. The method of claim 1, wherein the user interaction information comprises at least one of the group of: a slice and scroll pattern, change of a window level, a change of an image frame, an image orientation.

3. The method of claim 1, wherein the gaze tracking information comprises at least one of the group of: a fixation period, a viewing pattern, a region of interest.

4. The method of claim 1, further comprising:
   receiving, by the imaging device, further user input information corresponding to at least one of manipulations of the image and inputs on the first user interface; and
   adjusting the user interface further based upon the further user input information.

5. A device, comprising:
   a receiver configured to receive captured data;
   a processor configured to generate an image including identified areas;
   a display device configured to display the image; and
   a gaze tracker configured to collect gaze tracking information comprising a first viewing location on the image by a user of the device including determining of a starting point of a session or a new session, wherein the processor is further configured to determine one of the identified areas in the image being viewed based upon the viewing location, derive session state within a clinical context from at least a combination of two of: gaze tracking information and user interaction information, visual content analyses information; a user profile, interaction history, patient record data; determine a user interface to be provided based upon the determined identified area and the session state; display the user interface for use by the user on the display device, and capture user actions on the user interface over a period of time, wherein the user actions include instances where the user interface is used and unused, and wherein the user actions are used to determine the user interface for a further session.

6. The device of claim 5, wherein the user interaction information comprises at least one of the group of: a slice and scroll pattern, change of a window level, a change of an image frame, an image orientation.

7. The device of claim 5, wherein the faze tracking information further comprises at least one of the group of: a fixation period, a viewing pattern, a region of interest.

8. A Magnetic Resonance Imaging (MRI) device, comprising:
a capturing device configured to capture data of a patient based upon magnetic resonance information; and
an imaging device configured to receive the captured data to generate an image including identified areas on a display device thereof, wherein the imaging device includes a gaze tracker configured to track a viewing location on the image by a user of the imaging device, including determining a starting point of a session or a new session,
wherein the imaging device is further configured to determine one of the identified areas in the image being viewed based upon the viewing location, derive session state within a clinical context from at least a combination of two of: gaze tracking information and user interaction information, visual content analyses information; a user profile, interaction history, patient record data; determine a user interface to be provided based upon the determined identified area and the state information; display the user interface for use by the user on the display device and capture user actions on the user interface over a period of time, wherein the user actions include instances where the user interface is used and unused, and wherein the user actions are used to determine the user interface for a further session.

9. The Magnetic Resonance Imaging (MRI) device according to claim 8, wherein the user interaction information comprises at least one of the group of: a slice and scroll pattern, change of a window level, a change of an image frame, an image orientation.

10. The Magnetic Resonance Imaging (MRI) device according to claim 8, wherein the gaze tracking information further comprises at least one of the group of: a fixation period, a viewing pattern, a region of interest.

11. A method for supporting a visual image analysis, comprising:
receiving, by an imaging device including a gaze tracker, captured data used to generate an image that is displayed, the image including identified areas;
detecting a session based on at least one parameter selected from the group of: gaze tracking information, viewing settings, user interaction information, visual content analyses information; a user profile, interaction history and patient record data;
tracking, by the imaging device via the gaze tracker, a first viewing location on the image by the user of the imaging device;
analyzing information associated to the session to determine a clinical context of the session;
determining, by the imaging device, one of the identified areas in the image being viewed based upon the first viewing location;
determining, by the imaging device, a user interface based on the clinical context of the session;
displaying, by the imaging device, the user interface for use by the user; and
capturing user actions on the user interface over a period of time, wherein the user actions include instances where the user interface is used and unused, and wherein the user actions are used to determine the user interface for a further session.

\* \* \* \* \*